US012144689B2

(12) United States Patent
Govindaraj

(10) Patent No.: US 12,144,689 B2
(45) Date of Patent: Nov. 19, 2024

(54) DEVICE AND METHOD FOR GUIDING A NEEDLE TO A TARGET DURING AN INTERVENTIONAL PROCEDURE UNDER X-RAY IMAGING

(71) Applicant: Board of Regents, The University of Texas System, Austin, TX (US)

(72) Inventor: Ranganathan Govindaraj, Sugarland, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 49 days.

(21) Appl. No.: 17/405,775

(22) Filed: Aug. 18, 2021

(65) Prior Publication Data
US 2022/0054218 A1    Feb. 24, 2022

Related U.S. Application Data

(60) Provisional application No. 63/066,995, filed on Aug. 18, 2020.

(51) Int. Cl.
*A61B 90/11*    (2016.01)
*A61B 6/03*    (2006.01)
*A61B 90/00*    (2016.01)

(52) U.S. Cl.
CPC .............. *A61B 90/11* (2016.02); *A61B 6/032* (2013.01); *A61B 2090/3966* (2016.02)

(58) Field of Classification Search
CPC ............ A61B 90/11; A61B 2090/3966; A61B 2017/3405; A61B 17/3403; A61B 2017/3407; A61B 2017/3409; A61B 2090/376
See application file for complete search history.

(56) References Cited

U.S. PATENT DOCUMENTS

| | | | |
|---|---|---|---|
| 2015/0119753 A1* | 4/2015 | Cosgrove | A61B 5/4064 600/562 |
| 2015/0223901 A1* | 8/2015 | Wei | G16H 30/40 703/11 |
| 2016/0206383 A1* | 7/2016 | Leong | A61B 34/20 |
| 2017/0156751 A1* | 6/2017 | Csernatoni | A61B 17/8802 |
| 2018/0125528 A1* | 5/2018 | Page | A61B 17/34 |
| 2018/0368862 A1* | 12/2018 | Jain | A61B 90/50 |
| 2021/0085872 A1* | 3/2021 | Garcia Diaz | A61B 17/3403 |
| 2021/0322128 A1* | 10/2021 | Turner | A61B 90/10 |

FOREIGN PATENT DOCUMENTS

| CN | 107669318 A | * | 2/2018 | ............ A61B 1/01 |
|---|---|---|---|---|
| CN | 111297464 A | * | 6/2020 | |

* cited by examiner

*Primary Examiner* — Colin T. Sakamoto
*Assistant Examiner* — Tommy T Ly
(74) *Attorney, Agent, or Firm* — Thomas | Horstemeyer, LLP

(57) ABSTRACT

In one embodiment, a needle guide includes a guide element including a hollow body having a first opening at a first end, a second opening at a second end, and an interior space defined by an inner wall of the body that extends from the first opening to the second opening, wherein the second opening is smaller than the first opening and is configured to receive a needle having a tip that is to be positioned within a target site of a patient, and wherein the body includes a radiopaque material at the second opening that can be viewed during real-time medical imaging to facilitate placement and insertion of the needle.

10 Claims, 2 Drawing Sheets

DEVICE AND METHOD FOR GUIDING A NEEDLE TO A TARGET DURING AN INTERVENTIONAL PROCEDURE UNDER X-RAY IMAGING

CROSS-REFERENCE TO RELATED APPLICATION

This application claims priority to U.S. Provisional Application Ser. No. 63/066,995, filed Aug. 18, 2020, which is hereby incorporated by reference herein in its entirety.

BACKGROUND

In various interventional procedures, such as the administration of medication to a target site near the spine, medical imaging, such as fluoroscopy, is used during needle placement. When fluoroscopy is used as the imaging modality, an x-ray beam used to capture images of the target site and surrounding tissues is often magnified, which can make it more difficult to place the needle and increase the likelihood of injuring neighboring tissues, which can cause complications.

In view of the difficulties in placing a needle in such circumstances, it can be appreciated that it would be desirable to have a means for guiding a needle to a target site so as to assist a medical professional in reaching the target site with greater ease and without damaging neighboring tissues.

BRIEF DESCRIPTION OF THE DRAWINGS

The example embodiments can be best understood with reference to the accompanying figures. It is noted that that the various features illustrated in the figures are not necessarily drawn to scale. In those figures, like reference numerals refer to like features.

DETAILED DESCRIPTION

As described above, it would be desirable to have a means for guiding a needle to a target site while using real-time medical imaging so as to assist a medical professional in placing the tip of the needle in a target site within the body with greater ease and without damaging neighboring tissues. Disclosed herein are examples of such a means. More particularly, disclosed are needle guides through which a needle can be passed so as to position a tip of the needle in the target site. Once the needle tip is within the target site, one or more medications, such as analgesic medications, can be injected into the target site. In some embodiments, the needle guide comprises a guide element that is mounted to the distal end of a handle with which the needle guide can be held steady by a medical professional. In some embodiments, the guide element includes a radiopaque tip that is configured to be placed against the skin of the patient so that the tip can be viewed by the medical professional within a display or monitor during real-time imaging, such as fluoroscopy or computed tomography (CT). When the needle is passed through the guide element and into the patient, the guide element maintains the position of the needle relative to the patient and, therefore, prevents the needle from straying from the path to the target site. When the needle guide includes the handle, the medical professional can hold the guide element away from the injection site so as to avoid exposing his or her hand to radiation. Notably, because the needle tip can be positioned within the target site with greater ease when the needle guide is used, less time may be needed to place the needle, which reduces the amount of radiation to which the patient is exposed.

Figure 1:
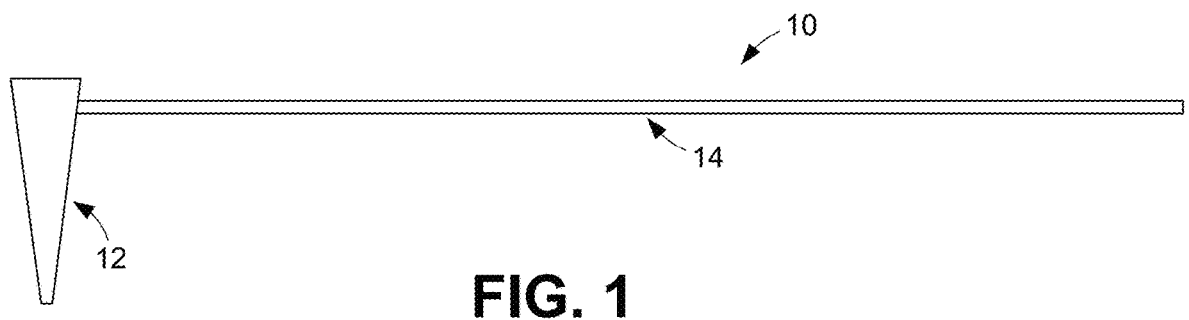
FIG. 1 is a side view of an embodiment of a needle guide.

FIG. 1 illustrates an example needle guide 10. In this example embodiment, the needle guide 10 generally includes a guide element 12 that is mounted to the end of an elongated handle 14. Although a handle 14 is shown in FIG. 1, it is noted that, in other embodiments, the handle can be omitted and the guide element 12 can be either held in place with one's hand or using a suitable armature.

Figure 2:
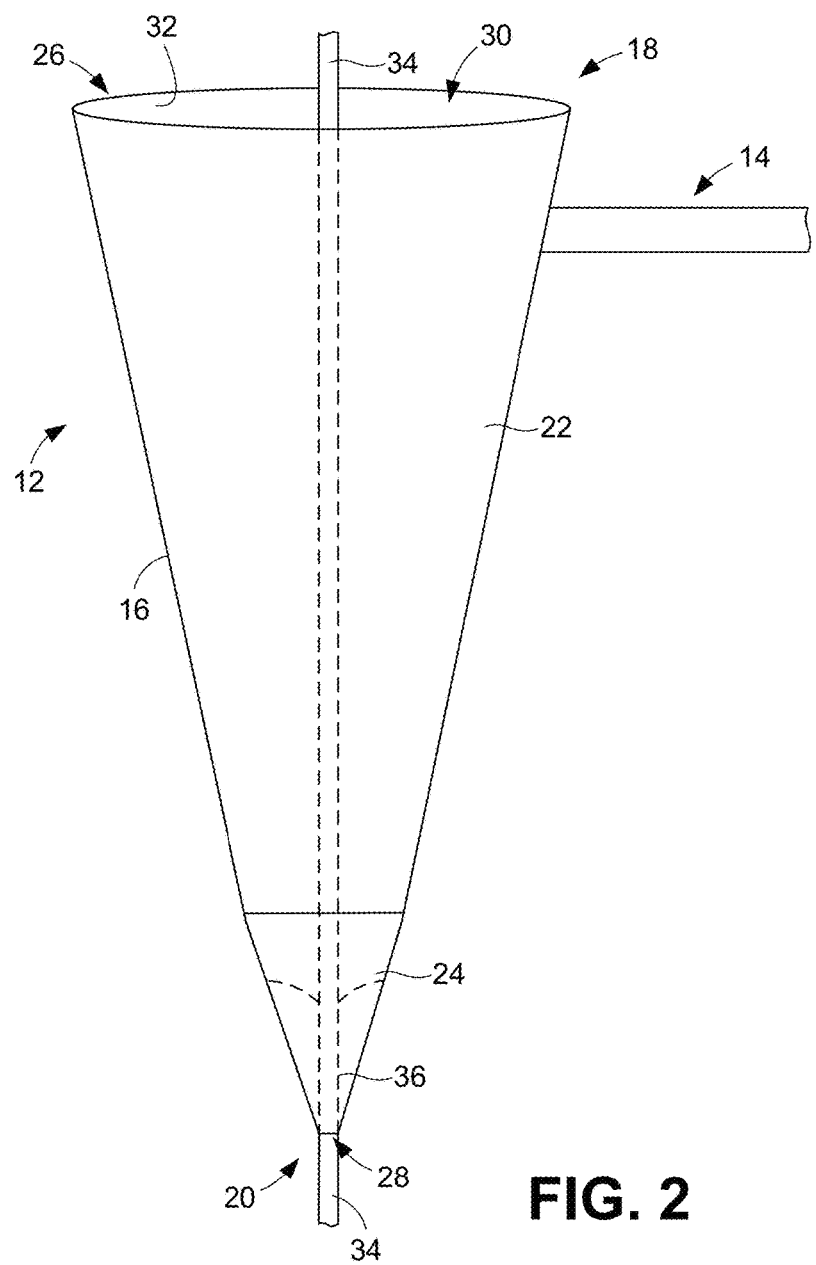
FIG. 2 is a detail view of the needle guide of FIG. 1, illustrating an embodiment for a guide element of the needle guide.

FIG. 2 illustrates an example embodiment for the guide element 12. As is apparent from this figure, the guide element 12 can have a body 16 that has a generally conical or frustoconical shape. In such a case, the body 16 has a circular cross-section (when taken perpendicularly to its axial direction) and tapers from a relatively wide upper end 18 to a relatively narrow lower end 20. In the example of FIG. 2, the body 16 comprises two distinct portions, including an upper portion 22 and a lower portion 24. The upper portion 22 forms a first or upper opening 26 while the lower portion 24 forms a second or lower opening 28. At least the upper portion 22 of the guide element 12 is hollow such that a generally conical or frustoconical interior space 30 is formed between the two openings 26, 28. That space is defined by one or more generally conical or frustoconical inner walls 32. The lower portion 24 can also be hollow and define its own generally conical or frustoconical interior space although, in some embodiments, at least the bottom portion of the lower portion at or near the lower opening 28 can be solid and form a bore 36 that extends a predetermined length along the lower portion to the lower opening so as to maintain a straight trajectory for a needle that is being guided.

In some embodiments, the lower portion 24, which forms a bottom tip of the guide element 12 that is configured to be placed against the patient's skin, is made of a radiopaque material, such as a metal material, while the upper portion 22 is made of a non-radiopaque material, such as a polymer or glass material, which can be translucent or transparent. Although the entirety of the lower portion 24 can be made of a radiopaque material, it is noted that, in some embodiments, only the very tip of the lower portion 24 (e.g., a ring surrounding the lower opening 28) can be made of a radiopaque material such that the lower portion comprises radiopaque material position at or near the lower opening. Irrespective of the particular construction of the lower portion 24, the radiopaque material of the lower portion will be clearly visible when positioned within the field of view of the medical imaging equipment (e.g., fluoroscopy or CT equipment) used during needle placement.

With further reference to FIG. 2, the needle guide 10 is shown in conjunction with a needle that it is guiding. In particular, a needle 34 has been passed through the upper opening 26, the interior space 30, and out through the lower opening 28 of the guide element 12.

In some embodiments, the guide element 12 can have dimensions that are particularly suited for specific sizes of needles. For example, the dimensions of the upper portion 22 and it's interior space 30, as well as the diameter of the lower opening 28, can be sized to receive specific needles. In some embodiments, the guide element 12 can be approximately 35 to 40 mm long (along it's axial direction), the upper opening can be approximately 6 to 8 mm in diameter, and the lower opening 28 can be approximately 2 to 4 mm in diameter. In embodiments in which the needle guide 10 includes the handle 14, the handle can be approximately 180 to 200 mm long.

Figure 3:
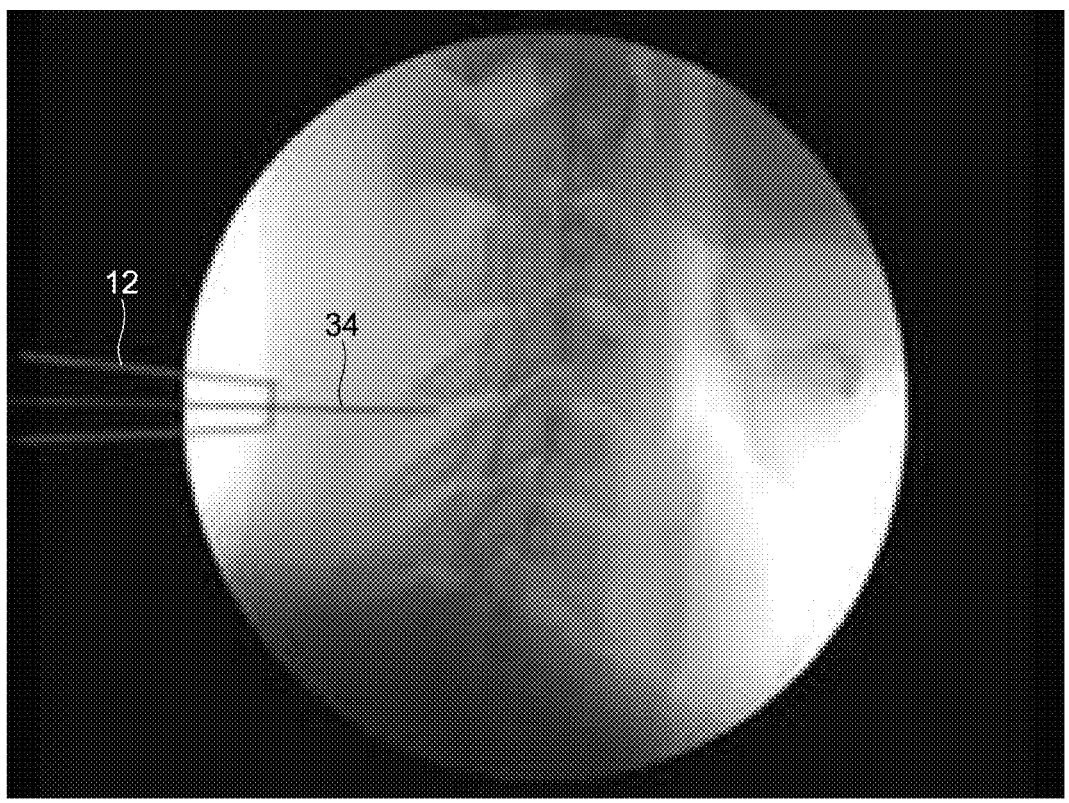
FIG. 3 is a fluoroscopy image that schematically illustrates use of a needle guide such as that illustrated in FIG. 1.

When a needle is to be guided to a target site within a patient, the bottom tip of the guide element 12 is positioned on the patient's skin in a location that aligns with the target site. Such alignment can be confirmed through real-time medical imaging, such as fluoroscopy or CT imaging. More particularly, the position of the tip can be confirmed by identifying the radiopaque material of the tip in a display or monitor of the fluoroscopy or CT equipment to ensure that the tip, and therefore the insertion point of the needle, is correctly aligned with the target site. FIG. 3 is a fluoroscopy image with a needle guide 12 and associated needle 34 schematically added to illustrate positioning and guiding of the needle to a target site within the spine. In some embodiments, correct alignment of the guide element 12 is achieved by positioning its radiopaque tip in a manner in which the needle will traverse a direct path to the target site that is generally parallel to the x-ray beam at an angle relative to the skin surface being dictated by the orientation of the guide element.

It is noted that the illustrative embodiments have been described with reference to a few embodiments for the purpose of demonstrating the principles and concepts of the invention. Persons of skill in the art will understand how the principles and concepts of the invention can be applied to other embodiments not explicitly described herein. For example, while a particular configuration of the current controller is described herein and shown in the figures, a variety of other configurations may be used. As will be understood by those skilled in the art in view of the description provided herein, many modifications may be made to the embodiments described herein while still achieving the goals of the invention, and all such modifications are within the scope of the invention.

What is claimed is:

1. A method for guiding a needle to a target site within a patient, the method comprising:
    performing real-time medical imaging of the patient and the target site;
    holding a needle guide element against the patient's skin using an elongated handle that extends outward from the needle guide element while capturing real-time images of the patient and the target site to confirm the needle guide element is positioned at a location on the skin surface that aligns with the target site, wherein the needle guide element comprises a body that includes a clear, conical or frustoconical, non-radiopaque upper portion defining an upper end of the guide element and a conical or frustoconical, radiopaque lower portion defining a lower end of the guide element, the body further including an upper opening provided at the upper end, a lower opening provided at the lower end, and an interior space that extends from the upper opening to the lower opening, wherein the lower opening is sized and configured to receive and guide the needle toward the target site; and
    after confirming correct placement of the needle guide element, passing a tip of the needle through the lower opening of the needle guide element, through the patient's skin, and into the target site while viewing the images of the patient and the target site as the needle guide element guides the needle to ensure it does not stray from a path that leads to the target site, wherein, because of the provision of the elongated handle, an operator holding the needle guide element can avoid being exposed to radiation associated with the real-time medical imaging.

2. The method of claim 1, wherein performing real-time medical imaging comprises performing fluoroscopy or computed tomography imaging.

3. A needle guide comprising:
    a guide element comprising a body that includes an upper portion defining an upper end of the guide element and a lower portion defining a lower end of the guide element, the upper portion being conical or frustoconical and being made of a transparent, non-radiopaque material and the lower portion being conical or frustoconical and being made of a radiopaque material, the body further including a first opening provided at the upper end, a second opening provided at the lower end, and an interior space that extends from the first opening to the second opening, the second opening being sized and configured to receive and guide a needle having a tip that is to be positioned within a target site of a patient; and
    an elongated handle having a distal end to which the guide element is mounted, wherein the guide element can be held against the patient in alignment with the target by an operator using the handle,
    wherein the radiopaque material can be viewed during real-time medical imaging to facilitate placement and insertion of the needle and wherein the handle enables the operator to hold the guide element in position during the real-time medial imaging without having to expose the operator's hand to radiation associated with the imaging.

4. The needle guide of claim 3, wherein the body of the guide element and its interior space tapers from the first opening to the second opening.

5. The needle guide of claim 3, wherein the lower portion of the guide element is made of a metal material.

6. The needle guide of claim 3, wherein the upper portion of the guide element is made of a polymer material.

7. The needle guide of claim 3, wherein the upper portion of the guide element is made of a glass material.

8. The needle guide of claim 3, wherein the lower portion of the guide element comprises a bore that is sized and configured to maintain a straight trajectory for the needle as it passes through the guide element and extends toward the target site.

9. The needle guide of claim 3, wherein the lower opening of the guide element is approximately 2 to 4 millimeters in diameter.

10. The needle guide of claim 9, wherein the upper opening of the guide element is approximately 6 to 8 millimeters in diameter.

* * * * *